US010568560B2

(12) United States Patent
Mukdadi et al.

(10) Patent No.: US 10,568,560 B2
(45) Date of Patent: Feb. 25, 2020

(54) ENDORECTAL PROSTATE PROBE WITH COMBINED PET AND US MODALITIES

(71) Applicants: Osama Mukdadi, Morgantown, WV (US); Mohamad W. Salkini, Morgantown, WV (US); Stanislaw Majewski, Morgantown, WV (US); James Proffitt, Newport News, VA (US)

(72) Inventors: Osama Mukdadi, Morgantown, WV (US); Mohamad W. Salkini, Morgantown, WV (US); Stanislaw Majewski, Morgantown, WV (US); James Proffitt, Newport News, VA (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 13/826,574

(22) Filed: Mar. 14, 2013

(65) Prior Publication Data
US 2014/0276018 A1   Sep. 18, 2014

(51) Int. Cl.
A61B 5/00    (2006.01)
A61B 8/00    (2006.01)
A61B 6/00    (2006.01)
A61B 8/12    (2006.01)
A61B 6/03    (2006.01)

(52) U.S. Cl.
CPC ............ *A61B 5/4381* (2013.01); *A61B 6/037* (2013.01); *A61B 6/4208* (2013.01); *A61B 6/4417* (2013.01); *A61B 8/12* (2013.01); *A61B 8/4416* (2013.01); *A61B 8/445* (2013.01)

(58) Field of Classification Search
CPC ..... A61B 5/4381; A61B 6/037; A61B 6/4208; A61B 6/4417; A61B 8/12; A61B 8/4416
See application file for complete search history.

(56) References Cited

U.S. PATENT DOCUMENTS

| 4,781,198 | A |   | 11/1988 | Kanabrocki |
| 4,930,515 | A | * | 6/1990 | Terwilliger .............. A61B 8/12 600/446 |
| 4,995,396 | A | * | 2/1991 | Inaba et al. ................... 600/431 |
| 5,014,708 | A |   | 5/1991 | Hayashi et al. |
| 5,170,055 | A |   | 12/1992 | Carroll et al. |

(Continued)

OTHER PUBLICATIONS

Greenlee, R.T., et al., Cancer Statistics, 2001. C Cancer J. Clin. 2001;51:15-36.

(Continued)

*Primary Examiner* — Amelie R Davis
(74) *Attorney, Agent, or Firm* — Buchanan Ingersoll & Rooney PC; Craig G. Cochenour, Esq.

(57) ABSTRACT

A dual modality probe is disclosed having both a positron emission tomography sensor and a ultrasound sensor. A dual imaging system is provided having the probe and at least one external positron emission tomography detector and a data acquisition computer system for collecting data simultaneously from the positron emission sensor and the ultrasound sensor of the probe and the positron emission tomography detector. A method for evaluating a target organ of a patient utilizing the probe and imaging system, and performing a biopsy of the organ is disclosed.

20 Claims, 13 Drawing Sheets

(56) References Cited

U.S. PATENT DOCUMENTS

| | | | |
|---|---|---|---|
| 5,776,062 | A | 7/1998 | Nields |
| 5,873,828 | A * | 2/1999 | Fujio et al. .................... 600/439 |
| 6,512,943 | B1 | 1/2003 | Kelcz |
| 6,546,279 | B1 | 4/2003 | Bova et al. |
| 6,951,542 | B2 | 10/2005 | Greppi et al. |
| 7,653,427 | B2 | 1/2010 | Essner et al. |
| 7,711,409 | B2 | 5/2010 | Keppel et al. |
| 7,894,876 | B2 | 2/2011 | von Rueckmann et al. |
| 2005/0171428 | A1* | 8/2005 | Fichtinger et al. ............ 600/426 |
| 2006/0237652 | A1* | 10/2006 | Kimchy ................... A61B 1/05 250/363.02 |
| 2007/0282221 | A1 | 12/2007 | Wang et al. |
| 2008/0128626 | A1* | 6/2008 | Rousso .................. A61B 5/418 250/362 |
| 2009/0030310 | A1* | 1/2009 | Hamill et al. ................ 600/437 |
| 2009/0030339 | A1* | 1/2009 | Cheng et al. .................. 600/562 |
| 2009/0112086 | A1* | 4/2009 | Melman ................. A61B 6/037 600/431 |
| 2009/0270760 | A1 | 10/2009 | Leimbach et al. |
| 2010/0187424 | A1* | 7/2010 | Majewski et al. ....... 250/363.05 |
| 2010/0198063 | A1 | 8/2010 | Huber et al. |
| 2011/0248175 | A1* | 10/2011 | Frach ................... G01T 1/2018 250/363.03 |
| 2011/0286576 | A1* | 11/2011 | Cui et al. ........................ 378/62 |

OTHER PUBLICATIONS

Ward, J.F. et al., "Radical Prostatectomy for clinically advanced (cT3) prostate cancer since the advent of prostate-specific antigen testing: 15-year outcome", BJU Int. 2005; 95:751-6.

Kupelian, P.. et al., "Year of treatment as independent predictor of relapse-free survival in patients with localized prostate cancer treated with definitive radiotherapy in the PSA era", Int. J Radiat Oncol Biol Phys. 2005; 63:795-9.

Huber, J.S., et al., "Initial Results of a Positron Tomograph for Prostate Imaging," TNS 53, 2006, pp. 2653-2659.

Turkington, T.G., et al., "PET Prostate Imaging with Small Planar Detectors," Medical Imaging Conference Record, 2004 IEEE vol. 5, Oct. 16-22, 2004, pp. 2806-2809.

Wu, H. et al., "Micro Insert: A Prototype Full-Ring PET Device for Improving the Image Resolution of a Small-Animal PET Scanner," The Journal of Nuclear Medicine, vol. 49, No. 10, Oct. 2008.

Tai, Y-C, "Virtual-pinhold PET." J Nucl Med 2008; 49:471-479.

Zhou, J. et al., "Theoretical Analysis and Simulation Study of a High-Resolution Zoom-in PET System," Phys. Med. Biol. 54 (2009): 5193-5208.

Huh, Sam S. et al. "Investigation of an Internal PET Probe for Prostate Imaging," Nuclear Instruments and Methods in Physics Research, Section A, 2007, vol. 579, No. 1, pp. 339-343.

Huber, J.S., et al., "Characterization of a PET Camera Optimized for Prostate Imaging," 2005 IEEE Nuclear Science Symposium Conference Record, vols. 1-5, 1:1556-9.

Huber, J.S., et al., "Dual-Modality PET/Ultrasound Imaging of the Prostate," http:/repositories.cdlib.org/lbnl/LBNL-59114.

Levin, C., "New Photon Sensor Technologies for PET in Prostate-Specific Imaging Configurations," presented at the Topical Symposium of Advanced Molecular Imaging Techniques in the Detection, Diagnosis, Therapy, and Follow-Up of Prostate Cancer, Dec. 6-7, 2005, Rome, Italy, http://www.iss.infn.it/congresso/prostate/presentations author.htm.

Moses, W., "Dedicated PET Instrumentation for Prostate Imaging," presented at the Topical Symposium on Advanced Molecular Imaging Techniques in the Detection, Diagnosis, Therapy, and Follow-Up of Prostate Cancer, Dec. 6-7, 2005, Rome, Italy, http://www.iss.infn.it/congresso/prostate/presentations author.htm.

Trabulsi, E. J., et al., Enhanced Transrectal Ultrasound Modalities in the Diagnosis of Prostate Cancer, doi:10.1016/j.urology.2010.05. 022.

Mullani et al., "First-Pass 18-F-FDG PET of Blood Flow," The Journal of Nuclear Medicine, vol. 49, No. 4, Apr. 2008.

Jadvar, H., "Prostate cancer: PET with 18F-FDG, 18F- or 11C-acetate, and 18F- or 11C-choline," Journal of Nuclear Medicine, vol. 52, pp. 81-89, Jan. 2011.

Krause, B.J. et al., "Imaging of prostate cancer with PET/CT and radioactively labeled choline derivates," Urol Oncol, vol. 29, Mar. 7, 2011.

Beheshti, L. et al., "F-18 Choline PET/CT in the Preoperative Staging of Prostate Cancer in Patients with Intermediate or High Risk of Extracapsular Disease: A Prospective Study of 130 Patients," Radiology, vol. 254, pp. 925-933, Mar. 2010.

Beattie, B.J. et al. "Pharmacokinetic Assessment of the Uptake of 16 beta-F-18-Fluoro-5 alpha-Dihydrotestosterone (FDHT) in Prostate Tumors as Measured by PET," Journal of Nuclear Medicine, vol. 51, pp. 183-192, Feb. 10, 2010.

Mease, R.C. et al., "N-[N-[(S)-1,3-dicarboxypropyl]carbamoyl]-4-[F-18]fluorobenzyl-L-cysteine, [F-18]DCFBC: A new imaging probe for prostate cancer," Clinical Cancer Research, vol. 14, pp. 3036-3043, May 15, 2008.

Peng, H. et al., "Recent Developments in PET Instrumentation," Current Pharmaceutical Biotechnology, vol. 11, pp. 555-571, Sep. 2010.

Levin, C. S., "New imaging technologies to enhance the molecular sensitivity of positron emission tomography," in Proceedings of the IEEE, 2008, pp. 439-467.

Lewellen, T. K., "The Challenge of Detector Designs for PET," American Journal of Roentgenology, vol. 195, pp. 301-309, Aug. 2010.

Soret, M. et al., "Partial-volume effect in PET tumor imaging," Journal of Nuclear Medicine, vol. 48, pp. 932-945, Jun. 2007.

Raylman, R. R. et al., "Initial clinical test of a breast-PET scanner," Journal of Medical Imaging and Radiation Oncology, vol. 55, pp. 58-64, Feb. 2011.

Raylman, R. R. et al., "The positron emission mammography/tomography breast imaging and biopsy system (PEM/PET): design, construction and phantom-based measurements," Physics in Medicine and Biology, vol. 53, pp. 637-653, Feb. 7, 2008.

Raylman, R. R. et al., "Quantification of radiotracer uptake with a dedicated breast PET imaging system," Medical Physics, vol. 35, pp. 4989-4997, Nov. 2008.

Sayed, A. et al., "Nonlinear characterization of breast cancer using multi-compression 3D ultrasound elastography in vivo (pending revision)," Ultrasonics, 2012.

Huber, J. S. et al., "Development of a PET-Transrectal Ultrasound Prostate Imaging System," IEEE Transactions on Nuclear Science, vol. 58, pp. 674-681, Jun. 2011.

Cespedes, I. et al., "Reduction of image noise in elastography," Ultrasonic Imaging, vol. 15, pp. 89-102, Apr. 1993.

Thitaikumar, A. et al., "Signal-to-noise ratio, contrast-to-noise ratio and their trade-offs with resolution in axial-shear strain elastography," Physics in Medicine and Biology, vol. 52, pp. 13-28, Jan. 7, 2007.

Zahiri-Azar, R. et al., "Motion estimation in ultrasound images using time domain cross correlation with prior estimates," IEEE Transactions on Biomedical Engineering, vol. 53, pp. 1990-2000, Oct. 2006.

Roncali, E. et al., "Application of Silicon Photomultipliers to Positron Emission Tomography," Annals of Biomedical Engineering, vol. 39, pp. 1358-1377, Apr. 2011.

Taghibakhsh, F. et al., "Silicon photomultipliers for positron emission tomography detectors with depth of interaction encoding capability," Nuclear Instruments & Methods in Physics Research Section a-Accelerators Spectrometers Detectors and Associated Equipment, vol. 633, pp. S250-S254, May 2011.

Delfino, E. P. et al., "Towards 1mm PET Resolution Using DOI Modules Based on Dual-Sided SiPM Readout," in 2010 IEEE Nuclear Science Symposium Conference Record (NSS/MIC), 2010, pp. 3442-3449.

Stolin, Alexander V. et al., "Construction and Evaluation of a Prototype High Resolution, Silicon Photomultiplier-Based, Tandem Positron Emission Tomography System", IEEE Transactions on Nuclear Science, vol. 60, No. 1, Feb. 2013, 82-86.

Majewski, S. et al., "Development of a "Resistive" Readout for SiPM Arrays," presented at the IEEE MIC conference, Valencia, Spain, 2011.

(56) References Cited

OTHER PUBLICATIONS

Proffitt, J. et al., "Implementation of a High-Rate USB Data Acquisition System for PET and SPECT Imaging," in 2006 IEEE Nuclear Science Symposium Conference Record, vol. 1-6, San Diego, 2006, pp. 3063-3067.

Proffitt, J. et al., "A flexible high-rate USB2 data acquisition system for PET and SPECT imaging," in 2005 IEEE Nuclear Science Symposium Conference Record, vols. 1-5, Puerto Rico, 2005, pp. 2971-2975.

McKisson, J. E. et al., "A Java distributed acquisition system for PET and SPECT imaging," in 2007 IEEE Nuclear Science Symposium Conference Record, vols. 1-11, 2007, pp. 3591-3593.

\* cited by examiner

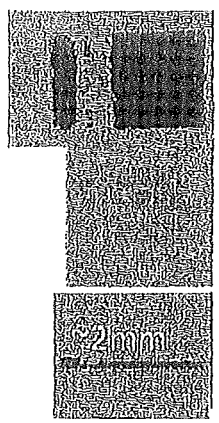 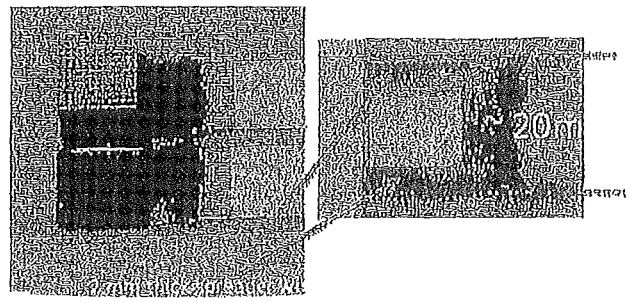
FIGURE 13 A	FIGURE 13 B

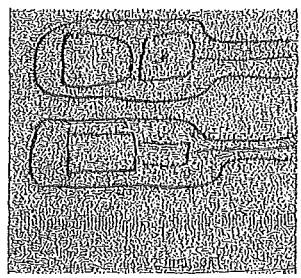 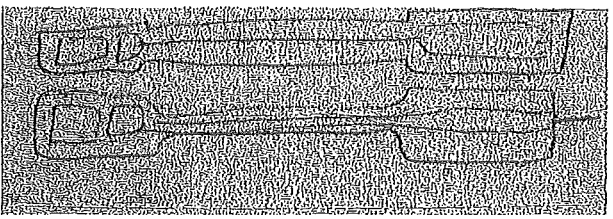
FIGURE 14 A    FIGURE 14 B

ENDORECTAL PROSTATE PROBE WITH COMBINED PET AND US MODALITIES

BACKGROUND OF THE INVENTION

Field of the Invention

The present invention relates to a device and method for performing hybrid imaging of organs and tumors. More particularly, an endorectal probe is provided for imaging of a prostate gland wherein the probe (device) has combined positron emission tomography and ultrasound imaging modalities.

Description of the Background Art

There are >200,000 new cases and nearly 30,000 deaths each year from prostate cancer (PCa) Prostate-specific antigen (PSA) testing has allowed early detection of impalpable PCa. Early detection has lowered the incidence of advanced disease with extracapsular extension and the subsequent early treatment appears to improve survival rate. After anomalous PSA results, the patient undergoes biopsy, and if the biopsy is positive, the patient undergoes surgery. The main objective of surgery is to remove the cancer at lowest functional cost, i.e. preserving continence and sexual function. The stage of the cancer decides the limits of the resection, and the larger the tumor the wider the excision needed, with radical prostatectomy as the limit of standard treatment. An accurate localization of the tumor and assessment of its size has two important advantages: it can direct the biopsy and can assist with the surgery. Biopsy results may be negative despite the presence of cancer due to sampling error. Prostate cancer is the only human cancer that does not have a standard method to image the primary tumor. The "blind" biopsy typically performed today under ultrasound (US) guidance results in high false negative diagnosis with many missed cancers. Accurate localization of the tumor, within the prostate and pelvic region, will better enable a tumor-free margin. Such accurate assessment today is not available with conventional imaging techniques [ultrasound (US), computed tomography (CT), magnetic resonance imaging and PET]. Standard PET scanners have spatial resolution inadequate to meet the clinical needs of prostate imaging—particularly when using specific, targeted imaging agents.

The diagnosis of prostate cancer is commonly based on a combination of digital rectal examination (DRE), serum prostate specific antigen (PSA) value, and transrectal ultrasound (TRUS) guided prostate biopsy findings. Conventional blind "biopsy" procedures under Tissue Differentiating Ultrasound are able to visualize only the structure and the margins of an organ, and thus do not provide differentiation between a cancerous tissue and healthy tissue.

Prostate cancer is the only human cancer that does not have a standard reliable method of imaging of the primary tumor. Functionally blind biopsy typically performed today under transrectal ultrasound guidance results in high false negative diagnoses with many missed cancers. Accurate localization of the tumor, within the prostate and pelvic region, will allow definition of a tumor-free margin. Such accurate assessment is generally not available in the present state of the art, with the conventional imaging techniques available to urologists.

The main problem is that prostate cancer is difficult to visualize in its early stage using current imaging technology. Conventional imaging modalities, such as ultrasound, CT (computed tomography) scan, and MRI (magnetic resonance imaging), can be used for the anatomic evaluation of prostate cancer. However, visible anatomic changes are not always present in early stages of the disease, making the use of current imaging modalities difficult in early detection of prostate cancer sites. The key problem with conventional guiding systems during prostate biopsy is that they are based on symmetrical anatomical sampling of the prostate, and not on the location of the cancer. The main challenge continues to be the inability to visualize the cancer in its early stages using current imaging technology.

U.S. Pat. No. 7,894,876 "Combined MR-optical coil for prostate, cervix, and rectum cancer imaging diagnostics" discloses a combined MR and optical system that may be used to guide a biopsy.

U.S. Pat. No. 7,711,409 "Opposed view and dual head detector apparatus for diagnosis and biopsy with image processing methods" discloses opposed gamma cameras for guiding a biopsy needle, but discloses no ultrasound imaging components.

U.S. Pat. No. 7,653,427 "Method and instrument for minimally invasive sentinel lymph node location and biopsy" discloses a radiation detector coupled with an ultrasound probe, for locating the position of a tagged tissue, and placement of a biopsy device.

U.S. Pat. No. 6,951,542 "Method and apparatus for ultrasound imaging of a biopsy needle or the like during an ultrasound imaging examination" discloses method including imaging and injection of contrast agents for placement of a biopsy device.

U.S. Pat. No. 6,546,279 "Computer controlled guidance of a biopsy needle" discloses a system for guiding a biopsy needle using one or more of computed tomography imaging, magnetic resonance, fluoroscopic imaging, or 3-D ultrasound imaging.

U.S. Pat. No. 6,512,943 "Combined ultrasound-radionuclide device for percutaneous ultrasound-guided biopsy and method of use" discloses a system and apparatus for performing tissue biopsy. An ultrasound imager and a "radionuclide detectors" are used, external to a patient, to locate "nuclear medicine tracer uptake" in the patient and generate superimposed images of an area of interest.

U.S. Pat. No. 5,776,062 "Enhanced breast imaging/biopsy system employing targeted ultrasound" discloses a system using X-ray imaging and ultrasound, external to a patient, to provide 3-D imaging of an area of interest for use with a biopsy procedure.

U.S. Pat. No. 5,170,055 "Radiation detecting biopsy probe" discloses a handheld biopsy probe that is guided by means of a scintillation crystal, but uses no ultrasound imaging. The device is used externally on a patient, as the primary application is for the detection of tumors in lymph nodes.

U.S. Pat. No. 5,014,708 "Radioactive ray detecting therapeutic apparatus" discloses a "radioactive ray guided" therapeutic device, where in one embodiment, the delivered therapy comprises destroying target cells by ultrasound, and removal of the cells by aspiration.

U.S. Pat. No. 4,995,396 "Radioactive ray detecting endoscope" discloses an endoscope having both an ultrasonic imaging device and a radioactive ray (e.g., beta radiation) detecting device in the tip of the endoscope, but does not disclose use of a biopsy device.

U.S. Pat. No. 4,781,198 "Biopsy tracer needle" discloses a method and device for obtaining a tissue sample, comprising a biopsy tracer needle (i.e., containing a radiation source) guided to a target tissue by means of an external scintillation device. No use of ultrasound is disclosed.

U.S. Published Application No. 2009/0270760 "Biopsy devices" discloses a biopsy device utilizing an isotopetagged needle mounted to a cradle support mechanism, where PET scanning is used to position the needle in a target tissue by manipulation of the cradle. No use of ultrasound is disclosed.

U.S. Published Application Serial No. 2007/0282221 "Ultrasound assist and X-ray assist biopsy devices" discloses a biopsy table, where a biopsy needle may be directed to a targeted tissue area by using an X-ray guided procedure for locating micro-calcifications, and using an ultrasound guided procedure for locating lesion masses.

U.S. Published Application Serial No. US 2010/0198063 A1 "Multi-Modality Of Phantoms And Methods For Co-Registration Of Dual PET-Transrectal Ultrasound Prostate Imaging" discloses use of a PET scanner and a transrectal ultrasound (TRUS) probe. The TRUS probe is inserted into the rectum of a patient for acquiring a TRUS image data of the prostate stepwise and then moving the patient bed to position the point sources near the external PET-center and acquiring the image, and then superimposing the PET image with the TRUS image for gaining a resulting image showing an anatomical and functional detail.

What is needed is a probe, and more specifically a prostate endorectal probe, and an imaging system, and method of evaluating a target organ of a patient, which overcomes the shortcomings of the present state of the art.

BRIEF SUMMARY OF THE INVENTION

The present invention fulfills the long an unmet needs of the health care clinician in evaluating a target organ of a patient.

In one embodiment of this invention, a dual modality probe is provided comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a positron emission tomography sensor located within the first end of the interior of the housing and wherein the positron emission tomography sensor is located in juxtaposition to the ultrasound sensor within the interior of the housing. Preferably, this dual modality probe includes wherein the ultrasound sensor is disposed within the interior of the housing such that it is rotatable about a first axis of rotation, and/or wherein the positron emission tomography sensor is disposed within the interior of the housing such that it is rotatable about a second axis of rotation. This probe also includes an ultrasound transmit/receive element disposed in juxtaposition to and in communication with said ultrasound sensor. Preferably, this probe includes a positron emission photoarray and a positron emission detection electronics each in juxtaposition to and in communication with the positron emission sensor. More preferably, the probe includes an electronic sensor positioning system located either on the exterior of the housing of the probe or within the interior of the housing wherein the electronic sensor positioning system is in communication with an outside (external) positron emission tomography imager.

In another embodiment of this invention, the probe, as described herein, includes an external shield that has a first end and a second end that is disposed opposite the first end, the external shield having an interior section, the interior section having a diameter that accommodates the probe of this invention being inserted into the interior section of the external shield, and wherein at least one of the first end or second end of the external shield is open such that the housing of the probe is freely movable within and outside of at least a portion of the external shield. Preferably, the housing of this probe is movable for at least one of a lateral movement, a longitudinal movement, or a transverse movement within and outside at least a portion of the external shield. More preferably, the probe is in communication with a movement element for controlling the lateral, or longitudinal, or transverse movements of the probe within and outside at least a portion of the external shield.

In a preferred embodiment of this invention, the probe is provided, as described herein, including wherein the ultrasound sensor is placed in front of the positron emission tomography sensor within the housing.

In a less preferred embodiment of this invention, the probe is provided, as described herein, wherein the ultrasound sensor is placed behind the positron emission tomography sensor within the housing. Optionally, in this less preferred embodiment of this invention, the probe includes an isolation compartment located within the housing for enclosing either partially or completely the ultrasound sensor within the housing from the positron emission tomography sensor.

In yet other embodiments of this invention, the probe, as described herein, includes wherein the ultrasound sensor and the positron emission tomography sensor are positioned on a support board within the housing of the probe. Other embodiments of the probe of this invention include wherein the ultrasound sensor, the positron emission tomography sensor, and the isolation compartment are positioned on a support board within the housing.

Another embodiment of the dual modality probe of this invention, as described herein, includes a biopsy gun attached to the external shell of the housing of the probe, the biopsy gun equipped with a biopsy needle.

In another embodiment of this invention, a mobile dual modality imaging system is provided comprising a bed for accommodating a patient, an open rotating gantry mounted around the bed and mobile with respect to the bed, a positron emission tomography imager having at least one mechanically separate positron emission tomography detector head secured to the rotating gantry above the bed and optionally at least one separate positron emission tomography detector head secured to the rotating gantry below the bed, wherein each of the detector heads are capable of angular rotation with respect to the bed to provide full angular projective sampling of a target organ of a patient lying on the bed, a probe (as described above, and herein) comprising at least an ultrasound sensor and a positron emission tomography sensor located in juxtaposition to each other, and an electronic sensor positioning system located on or in the probe and on or within each of the positron emission tomography detector heads such that the electronic sensor positioning system is in communication with the positron emission detector heads and the positron emission tomography sensor of the probe for spatially co-registering the probe to each detector head and for controlling an absolute and relative positioning of the probe, the positron emission tomography imager, and a target organ of a patient, and a data acquisition computer system for collecting data simultaneously from the positron emission sensor and the ultrasound sensor of the probe and the positron emission tomography imager. In another embodiment of this invention, the imaging system, as described herein includes wherein the probe includes an ultrasound transmit/receive element disposed in juxtaposition to and in communication with the ultrasound sensor of the probe.

In a preferred embodiment of this invention, the dual modality imaging system, as described herein, includes the probe, as described herein, which further includes a positron emission photoarray and a positron emission detection electronics each in juxtaposition to and in communication with the positron emission sensor.

Another embodiment of this invention provides for the imaging system, as described herein, wherein the detector heads are capable of being operated in a static mode in which each of the detector heads are fixed in position with respect to a target organ of a patient lying on the bed, or in a dynamic mode in which each of the detector heads are rotated with respect to the target organ of the patient lying on the bed to provide full angular projective sampling of the target organ for enhanced tomographic 3D reconstruction, and wherein the detector heads can be rotated to a new viewing angle with respect to the target organ and then operated in the static mode to better view the target organ of the patient lying on the bed and to optimize positron emission tomographic 3D spatial resolution. Preferably, the rotating gantry of the imaging system enables 360 degree angular sampling in a 3D imaging mode with the probe and the positron emission tomography imager. Most preferably, the dual modality imaging system as described herein includes wherein the ultrasound sensor is placed in front of the positron emission tomography sensor within the housing of the probe. In a less preferred embodiment of this invention, the dual modality imaging system includes the probe, as described herein, wherein the ultrasound sensor is placed behind the positron emission tomography sensor within the housing of the probe. In this less preferred embodiment, it is advisable to include an isolation compartment located within the housing of the probe for enclosing either partially or completely the ultrasound sensor within the housing from the positron emission tomography sensor.

In another embodiment of this invention, the imaging system includes the probe, as described herein, having the ultrasound sensor and the positron emission tomography sensor of the probe positioned on a support board within the housing of the probe.

In yet another embodiment of this invention, the imaging system includes the probe, as described herein, having the ultrasound sensor, the positron emission tomography sensor, and the isolation compartment of the probe positioned on a support board within the housing of the probe.

Another embodiment of this invention provides for a method for evaluating a target organ of a patient. This method comprises injecting a patient with an imaging agent, providing a mobile dual modality imaging system, as described above and herein, and operating the dual modality imaging system such that said dual modality imaging system is positioned to scan a target organ of the patient. It will be appreciated that operating the dual modality imaging system includes inserting the probe of the imaging system into a cavity of the patient that is in proximity to the target organ under evaluation. For example, the probe of the imaging system is inserted into the rectum of a patient for evaluating rectal tissue of the colon or for evaluating the prostate gland of a male patient.

Another embodiment of the method of the present invention includes providing the imaging system with a probe, as described herein, having an optional biopsy gun positioned on the external shell of the housing of the probe for conducting a biopsy of the target organ.

The additional features and advantage of the disclosed invention is set forth in the detailed description which follows, and will be apparent to those skilled in the art from the description or recognized by practicing the invention as described, together with the claims and appended drawings.

BRIEF DESCRIPTIONS OF THE DRAWINGS

The foregoing aspects, uses, and advantages of the present invention will be more fully appreciated as the same becomes better understood from the following detailed description of the present invention when viewed in conjunction with the accompanying figures.

Figure 12:
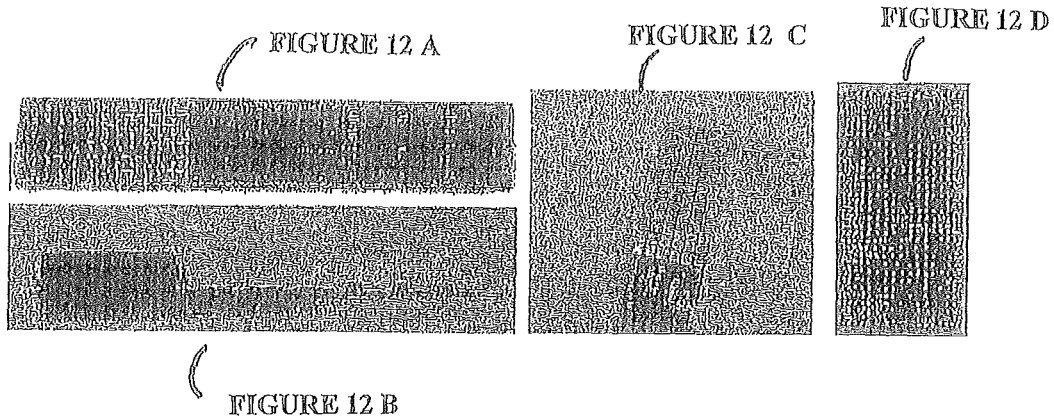

FIG. 12A shows an embodiment of the PET photodetector (PET sensor) built of 72 MPPCs units arranged in a 6×12 array. FIG. 12 B shows a side view of the probe with a 1 cm thick LYSO array. FIG. 12 C shows an embodiment of the probe of this invention and its components including a light spreader window which provides light sharing between individual MPPC units and a LYSO array of 1.5×1.5×10 mm pixels. FIG. 12D shows a raw image obtained with the LYSO array coupled to to the MPPC array.

FIG. 13A shows another embodiment of the probe of the present invention that is 14 mm (millimeter) wide having a high resolution (1 mm) with a depth of interaction (DOI) capability, a 12×12 pixel LYSO scintillator array with 50 micron Lumirror septa for DOI operation, coupled to a <2 mm thick SensL 16ch SPMArray2 module (shown in the bottom image of FIG. 13 A). FIG. 13B shows a 1 mm DOI module during assembly with two SiPM modules coupled at both sides of the LYSOarray.

Figure 15:
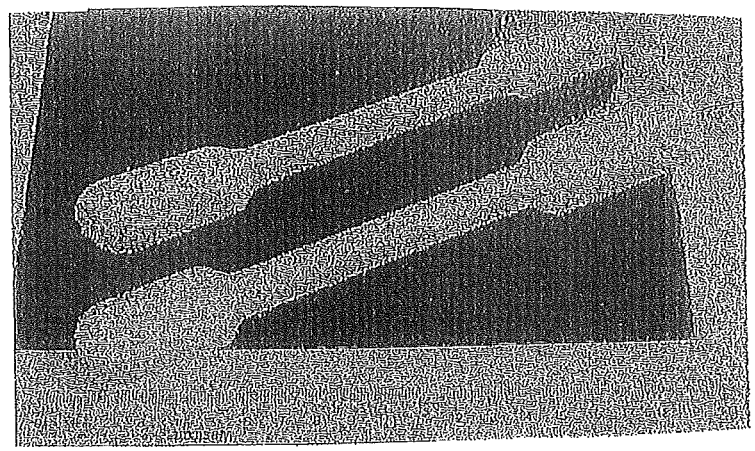

FIG. 14 A, FIG. 14B, and FIG. 15 show assembled dual modality probes of the present invention.

Figure 16:
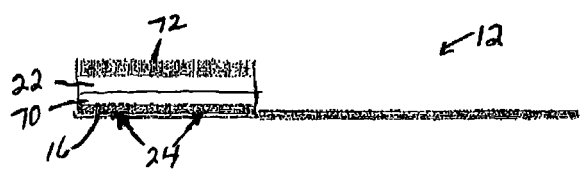

FIG. 16 is a cross-sectional view of a positron emission tomography sensor.

Figure 17:
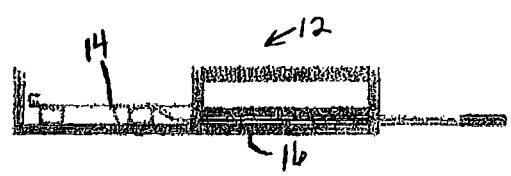

FIG. 17 is a cross-sectional view of the positron emission tomography sensor of FIG. 16 disposed adjacent an ultrasound sensor.

Figure 18:
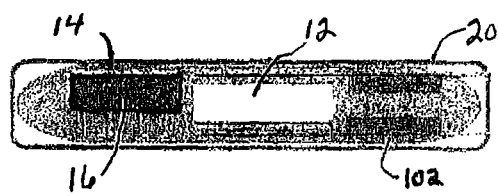

FIG. 18 is a cross-sectional view of a prostate endorectal probe having a positron emission tomography sensor, an ultrasound sensor, and a detection/control electronics.

Figure 7:
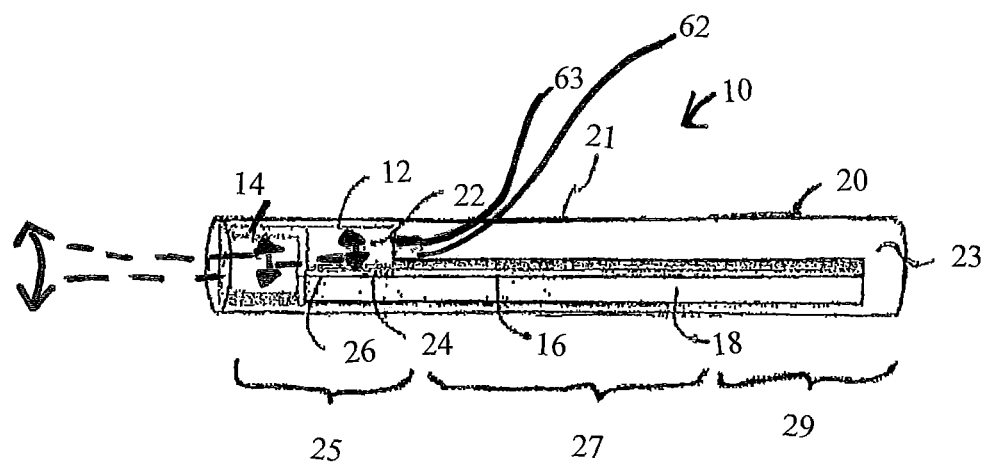
FIG. 7 is a side view of an embodiment of the probe of the present invention wherein the ultrasound sensor is placed in front of the PET sensor of the probe.
Figure 19:
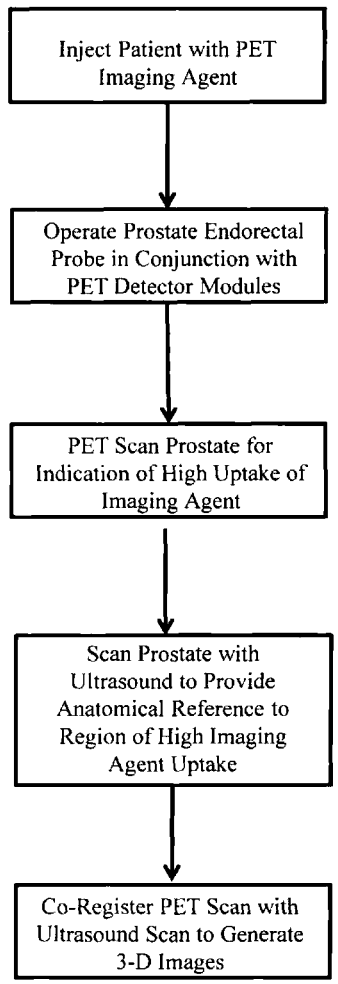

FIG. 19 is a flow chart illustrating an embodiment of the method of the present invention of evaluating a target organ using the prostate endorectal probe of FIG. 7 and the imaging system of this invention.

DETAILED DESCRIPTION OF THE INVENTION

The positron emission tomography and ultrasound dual modality probe and dual modality imaging system of this invention provide significant improvement over existing devices and methods to obtain evaluations of a target organ of a patient, a biopsy of the target organ, and to perform localized surgery of the target organ. The target organ may be, for example, but not limited to the prostate gland of a male patient, a gynecological anatomical structure of a female patient (vagina, cervix, uterus, etc.), or the rectum of a patient, or other anatomical structure of a patient wherein an endoscopic probe is utilized.

In a preferred embodiment of this invention, the probe and imaging system and method of this invention is useful to guide prostate biopsy/surgery with high resolution combined dual-modality (hybrid) PET (Positron Emission Tomography) probe/US (Ultrasound) probe imaging in one compact endorectal device. The 3D images from the two modalities are naturally fused because the corresponding images are obtained at the same time and at the same probe position.

The probe and imaging system of the invention is a novel dedicated high resolution probe system. The ultrasound sensor element has enhanced ultrasound features allowing for prostate tissue differentiation in addition to its structural imaging and in addition to the molecular differentiation (of the cancerous from benign) tissues of the positron emission tomography sensor element. Combined spectroscopic power of these two modalities (PET/US) offers unique tissue differentiation on top of anatomic guidance offered by the standard TRUS (transrectal ultrasound) technique. Optionally, the probe and imaging system of this invention include a temperature probe, position and angle locator, as well as enhancements, described herein, to the basic operational parameters.

In a preferred embodiment of this invention, the method of the present invention utilizes the dual modality probe and the imaging system so that prostate biopsy can be performed accurately, which at the present time many of such biopsies of the prostate are poor at best.

The dual modality (hybrid) probe of this invention comprises in one housing both Ultrasound (US) and Positron Emission Tomography (PET) modalities. The US component will provide the usual structural 3D information, as the standard TransRectal Ultrasound (TRUS) probe, and a PET probe. The imaging system comprises the probe of this invention, operating with an external coincident PET module or set of modules in different configurations that will provide the metabolic information related to the biological state of the target organ, such as for example, the prostate gland, and specifically about the presence of any cancerous structures exhibiting increased metabolic activity. In addition to cancer diagnosis, the dual-modality PET/US prostate probe and imaging system can be used in biopsy and in surgical guidance.

In one embodiment of this invention, a dual modality probe is provided comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a positron emission tomography sensor located within the first end of the interior of the housing and wherein the positron emission tomography sensor is located in juxtaposition to the ultrasound sensor within the interior of the housing. Preferably, the dual modality probe, as described herein, includes wherein the ultrasound sensor is disposed within the interior of the housing such that it is rotatable about a first axis of rotation, and/or wherein the positron emission tomography sensor is disposed within the interior of the housing such that it is rotatable about a second axis of rotation. The probe also includes an ultrasound transmit/receive element disposed in juxtaposition to and in communication with said ultrasound sensor. Preferably, the probe, as described herein, includes a positron emission photoarray and a positron emission detection electronics each in juxtaposition to and in communication with the positron emission sensor. More preferably, the probe, as described herein, includes an electronic sensor positioning system located either on said exterior of said housing of said probe or within said interior of said housing wherein said electronic sensor positioning system is in communication with an outside positron emission tomography imager.

In another embodiment of this invention, the probe, as described herein, includes an external shield that has a first end and a second end that is disposed opposite said first end, said external shield having an interior section, said interior section having a diameter that accommodates the probe of this invention being inserted into the interior section of the external shield, and wherein at least one of the first end or second end of the external shield is open such that the housing of the probe is freely movable within and outside of at least a portion of the external shield. Preferably, the housing of the probe of this invention, as described herein, is movable for at least one of a lateral movement, a longitudinal movement, or a transverse movement within and outside at least a portion of the external shield. More preferably, the probe is in communication with a movement element for controlling the lateral, or longitudinal, or transverse movements of the probe within and outside at least a portion of the external shield. The movement element may be for example but not limited to a mechanical stepper device as know by those persons skilled in the art, or a motorized unit that is controlled by computer processor.

In a preferred embodiment of this invention, the probe is provided, as described herein, including wherein the ultrasound sensor is placed in front of the positron emission tomography sensor within the housing.

In a less preferred embodiment of this invention, the probe is provided, as described herein, wherein the ultrasound sensor is placed behind the positron emission tomography sensor within the housing. Optionally, in this less preferred embodiment of this invention, the probe includes an isolation compartment located within the housing for enclosing either partially or completely the ultrasound sensor within the housing from the positron emission tomography sensor.

In yet other embodiments of this invention, the probe, as described herein, includes wherein the ultrasound sensor and the positron emission tomography sensor are positioned on a support board within the housing of the probe. Other embodiments of the probe of this invention include wherein the ultrasound sensor, the positron emission tomography sensor, and the isolation compartment are positioned on a support board within the housing.

Another embodiment of the dual modality probe of this invention, as described herein, includes a biopsy gun attached to the external shell of the housing of the probe, the biopsy gun equipped with a biopsy needle.

In another embodiment of this invention, a mobile dual modality imaging system is provided comprising a bed for accommodating a patient, an open rotating gantry mounted around the bed and mobile with respect to the bed, a positron emission tomography imager having at least one mechanically separate positron emission tomography detector head secured to the rotating gantry above the bed and optionally at least one separate positron emission tomography detector head secured to the rotating gantry below the bed, wherein each of the detector heads are capable of angular rotation with respect to the bed to provide full angular projective sampling of a target organ of a patient lying on the bed, a probe comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a positron emission tomography sensor located within the first end of the interior of the housing and wherein the positron emission tomography sensor is located in juxtaposition to the ultrasound sensor within the interior of the housing, an electronic sensor positioning system located either on the exterior of the housing of the probe or within the interior of the housing and on or within each of the positron emission tomography detector heads such that the electronic sensor positioning system is in communication with the positron emission detector heads and the positron emission tomography sensor of the probe for spatially co-registering the probe to each detector head and for controlling an absolute and relative positioning of the probe, the positron emission tomography imager, and a target organ of a patient, and data acquisition computer system for collecting data simultaneously from the positron emission sensor and the ultrasound sensor of the probe and the positron emission tomography imager. Preferably, the imaging system, as described herein, includes wherein the ultrasound sensor of the probe is disposed within the interior of the housing such that it is rotatable about a first axis of rotation. Preferably, the imaging system, as described herein, includes wherein the positron emission tomography sensor of the probe is disposed within the interior of the housing such that it is rotatable about a second axis of rotation. More preferably, the imaging system, as described herein, includes wherein the ultrasound sensor of the probe is disposed within the interior of the housing such that it is rotatable about a first axis of rotation and wherein the positron emission tomography sensor is disposed within the interior of the housing such that it is rotatable about a second axis of rotation. In another embodiment of this invention, the imaging system, as described herein includes wherein the probe includes an ultrasound transmit/receive element disposed in juxtaposition to and in communication with the ultrasound sensor of the probe.

In a preferred embodiment of this invention, the dual modality imaging system, as described herein, includes the probe, as described herein, which further includes a positron emission photoarray and a positron emission detection electronics each in juxtaposition to and in communication with the positron emission sensor.

Another embodiment of this invention provides for the imaging system, as described herein, wherein the detector heads are capable of being operated in a static mode in which each of the detector heads are fixed in position with respect to a target organ of a patient lying on the bed, or in a dynamic mode in which each of the detector heads are rotated with respect to the target organ of the patient lying on the bed to provide full angular projective sampling of the target organ for enhanced tomographic 3D reconstruction, and wherein the detector heads can be rotated to a new viewing angle with respect to the target organ and then operated in the static mode to better view the target organ of the patient lying on the bed and to optimize positron emission tomographic 3D spatial resolution. Preferably, the rotating gantry of the imaging system enables 360 degree angular sampling in a 3D imaging mode with the probe and the positron emission tomography imager. Most preferably, the dual modality imaging system as described herein includes wherein the ultrasound sensor is placed in front of the positron emission tomography sensor within the housing of the probe. In a less preferred embodiment of this invention, the dual modality imaging system includes the probe, as described herein, wherein the ultrasound sensor is placed behind the positron emission tomography sensor within the housing of the probe. In this less preferred embodiment, it is advisable to include an isolation compartment located within the housing of the probe for enclosing either partially or completely the ultrasound sensor within the housing from the positron emission tomography sensor.

In another embodiment of this invention, the imaging system includes the probe, as described herein, having the ultrasound sensor and the positron emission tomography sensor of the probe positioned on a support board within the housing of the probe.

In yet another embodiment of this invention, the imaging system includes the probe, as described herein, having the ultrasound sensor, the positron emission tomography sensor, and the isolation compartment of the probe positioned on a support board within the housing of the probe.

Another embodiment of this invention provides for a method for evaluating a target organ of a patient. This method comprises injecting a patient with an imaging agent, providing a mobile dual modality imaging system comprising a bed for accommodating a patient, an open rotating gantry mounted around the bed and mobile with respect to the bed, a positron emission tomography imager having at least one mechanically separate positron emission tomography detector head secured to the rotating gantry above the bed and optionally at least one separate positron emission tomography detector head secured to the rotating gantry below the bed, wherein each of the detector heads are capable of angular rotation with respect to the bed to provide full angular projective sampling of a target organ of a patient lying on the bed, a probe comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a positron emission tomography sensor located within the first end of the interior of the housing and wherein the positron emission tomography sensor is located in juxtaposition to the ultrasound sensor within the interior of the housing, an electronic sensor positioning system located either on the exterior of the housing of the probe or within the interior of the housing and on or within each of the positron emission tomography detector heads such that the electronic sensor positioning system is in communication with the positron emission detector heads and the positron emission tomography sensor of the probe for spatially co-registering the probe to each detector head and for controlling an absolute and relative positioning of the probe, the positron emission tomography imager, and a target organ of a patient, and a data acquisition computer system for collecting data simultaneously from the positron emission sensor and the ultrasound sensor of the probe and the positron emission tomography image, positioning the patient on the bed of the dual modality imaging system, and operating the dual modality imaging system such that said dual modality imaging system is positioned to scan a target organ of the patient. It will be appreciated that operating the dual modality imaging system includes inserting the probe of the imaging system into a cavity of the patient that is in proximity to the target organ under evaluation. For example, the probe of the imaging system is inserted into the rectum of a patient for evaluating rectal tissue of the colon or for evaluating the prostate gland of a male patient.

Another embodiment of the method of the present invention includes providing the imaging system with a probe, as described herein, having an optional biopsy gun positioned on the external shell of the housing of the probe for conducting a biopsy of the target organ.

A preferred embodiment of the method of the present invention is set forth below. Before a prostate biopsy is performed, the method of evaluating the prostate gland and any region of interest (ROI) thereof is performed. The patient will be injected systemically into a vein with a PET imaging agent targeting the prostate or a ROI of the prostate know to have cancer. During this procedure, the PET/US probe operating with the external PET imager modules (see attached Figures) will be used to scan the region of the prostate for any signs of unusually high uptake of the PET imaging agent, reflecting the presence of a potentially cancerous structure/lesion. US scan will provide an anatomical reference to the PET image. The two 3D volumes of both modality images will be co-registered and fused to produce sets of any desired planar images of the tissue layers for definition where the hot spots/lesions are located. This in turn can provide guidance for biopsy and for surgery if the surgery needed. If the patient undergoes surgery for a positive biopsy result, the prostate will be examined closely for correlation with the PET-US finding. In addition, the US probe can be equipped with enhanced US features or modalities, such as 3D operation, color and power Doppler, contrast-enhancement, harmonic and flash replenishment imaging, and elastography, as some examples. As noted above, for example, the dual modality PET/US imaging system can have also applications in gynecological exams and potentially also in colon exams.

Figure 1:
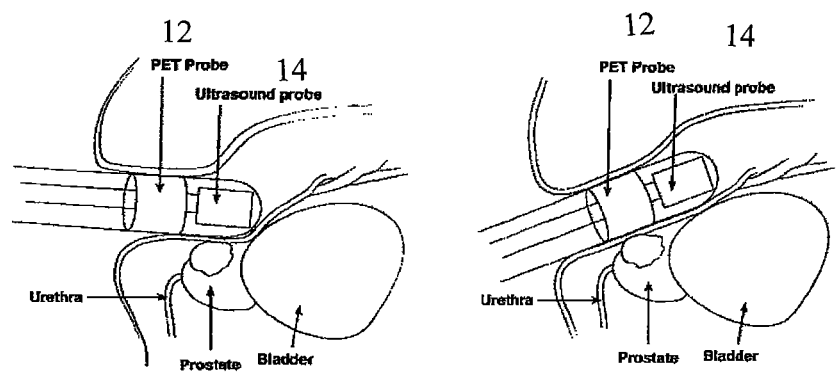
FIG. 1 shows the prostate dual modality endorectal probe, of this invention, having an ultrasound sensor disposed at the forward end of the housing of the probe and a PET sensor within the housing of the probe and located behind the ultrasound sensor. The probe is inserted into the rectum of a male patient during an imaging phase of the method of the present invention.
Figure 2:
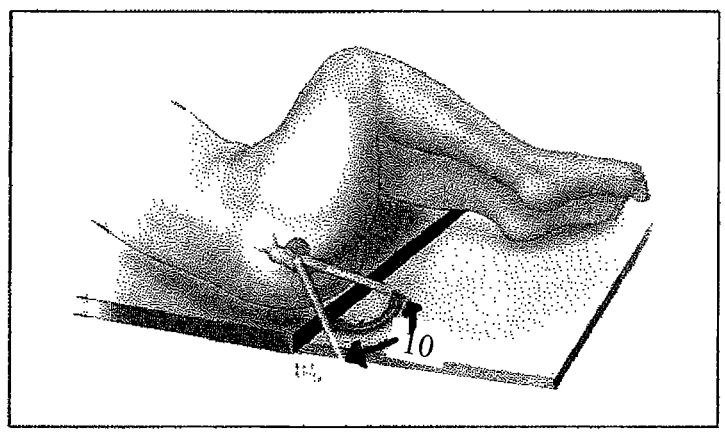
FIG. 2 shows the probe of this invention inserted into the rectum of a male patient at varying angles for better alignment with the prostate gland.
Figure 3:
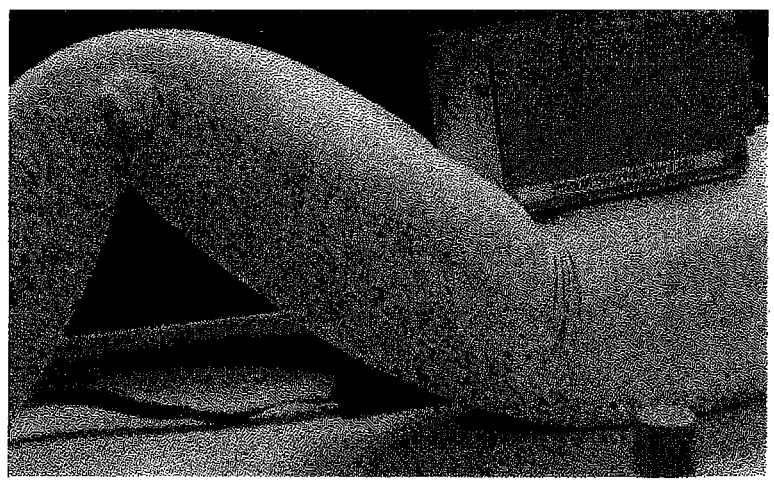
FIG. 3 shows an embodiment of the imaging system of the present invention wherein one PET imaging detector is placed above the patient and operating in coincidence with the probe (not shown) of this invention.

FIG. 1 shows a preferred embodiment of the dual—modality probe of the present invention inserted into the rectum of a patient for ultrasound imaging (US sensor placed in front of the PET sensor within the probe housing). FIG. 1A shows the probe inserted into to rectum during the ultrasound imaging phase. By pushing the probe more inside the rectum (ie. further into the rectum) and changing the angle (FIG. 1B) the PET sensor of the probe will come closer to the prostate gland for optimal PET imaging. FIG. 2 shows a patient on his side with the probe inserted into the rectum. By changing angle of the probe, the ultrasound and PET sensors can be better aligned with the prostae gland. One or more PET imaging detector or detectors (not shown in FIG. 2, but shown in FIG. 3) is placed in front of the patient. The PET imaging detector operates in co-incidence with the probe.

Figure 4:
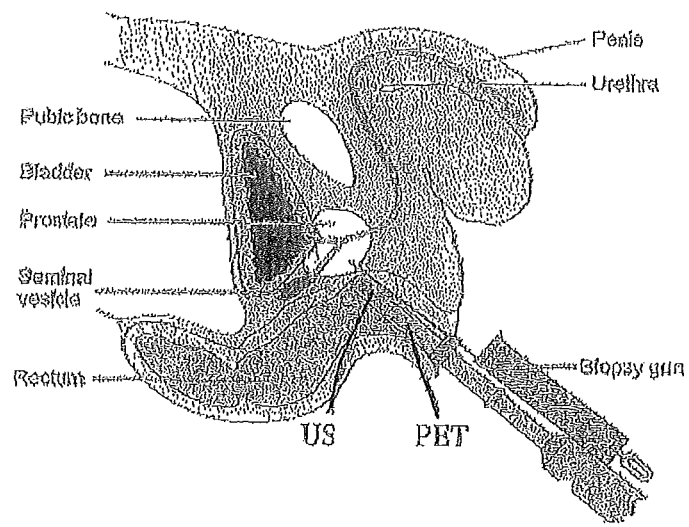
FIG. 4 shows an embodiment of the dual modality probe of this invention wherein the ultrasound sensor is placed in front of the positron emission tomographic sensor (PET sensor) and the optional biopsy gun with needle attached to the external housing of the probe. The probe is inserted into the rectum of a male patient.

FIG. 4 shows the dual modality probe of this invention equipped with an optional biopsy gun for performing a biopsy if after identifying suspicious lesions based upon the PET/US results concerning elasticity characteristics. The ultrasound component of the probe will then be used to guide the needle of the biopsy gun based upon the established dual modality PET-US scan of the target organ, here for example, the prostate gland.

A preferred embodiment of the probe of the present invention includes an (i) ultrasound component having a an ultrasound (US) element (emitter+receiver) with control/readout box, (ii) a PET sensor (scintillator+SiPM [silicon photomultiplier] photodetector), (iii) a 6 degrees of freedom (3 coordinates and 3 angles) positioning sensor with readout, (iv) Fusion algorithms and software, fusing the PET and US modalities in 3D and in 2D projections for viewing and guidance, and optionally (v) one or more temperature sensors with bias voltage feedback for the PET probe. Further, the probe of the present invention may optionally include the following elements: (i) a fast signal electronics implementation of the PET sensor for the Time of Flight (TOF) capability, (ii) 3D US operation, (iii) US elastography, (iv) 3D US operation, (v) US elastography, (vi) US color and power Doppler, (vii) contrast-enhancement, harmonic and flash replenishment imaging, etc., and (viii) an optical sensor (visible, UV, IR) with spectrum analyzer.

The preferred technology of the PET probe is a combination of compact Silicon Photomultipliers (SiPMs) and pixellated scintillators. The scintillators detect the 511 keV annihilation gammas from positron emissions in the prostate and surroundings and convert the detected energy into scintillation signals which are in turn detected in the SiPM photodetectors.

The external PET panel detectors can be built using different combinations of photodetectors and scintillators. In a preferred embodiment of the PET detectors, the panel detectors are position sensitive photomultipliers and pixellated scintillators. The outer PET detectors can take different forms, from full rings to simple panels.

The ultrasound sensor comprises a 2D array piezoelectric material that provides 3D ultrasound images. The 2D piezoelectric array is diced into pillars to generate ultrasound beams. The probe will also consist of a backing layer and two matching layers to broaden the frequency spectrum and therefore improve the image resolution. The probe can operate at a frequency range from 2.5 MHz up to 15 MHz. The 2D array probe will be able to steer in different angles to generate ultrasound beams along different directions. The field of view ranging from 30 mm to 150 mm can be controlled by clinicians to image a specific region of interest (ROI) of a target organ. Additionally, this ultrasound technology will be equipped with B-mode, M-mode, and color Doppler techniques to ease interpretation of ultrasound images and provide information on blood flow circulations.

Advanced image and signal processing techniques for tissue classifications will be implemented on radiofrequency echoes obtained from prostate cancer. Signal processing analyses in time-, frequency-, and wavelet-domains can be performed to detect tissue abnormalities of prostate cancer tissues. The 3D ultrasound images can be extracted and fused with PET images for enhanced image visualization.

Figure 5:
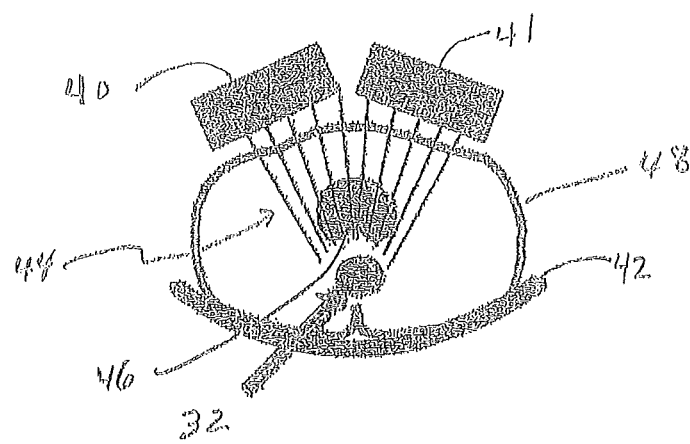
FIG. 5 is a cross-sectional view of an embodiment of the imaging system of the present invention showing the prostate endorectal probe operating in conjunction with two PET imaging detector panels placed stereotactically above the patient.

FIG. 5 shows an embodiment of this invention wherein the probe having the ultrasound and PET sensors of the probe that is further partially enveloped in the external shield is inserted into the rectum of a patient and two PET imaging panels placed stereotactically above the patient and operating in co-incidence with the PET sensor element of the probe of this invention. To immobilize the prostate during the dual modality imaging system scan of this invention, the wall of the external shield (having a larger diameter than the diameter of the probe of this invention) is used to immobilize the prostate during the whole imaging system procedure or method of the present invention. During the imaging system scan, the probe of this invention is moved inside the external shield longitudinally and transversely to cover the necessary volume of the prostate for both the ultrasound and the positron emission tomography scans.

Figure 6:
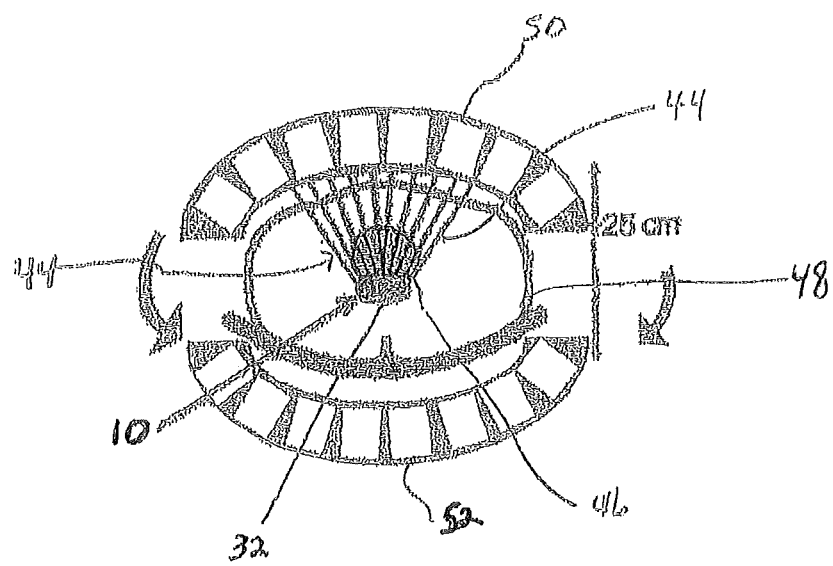
FIG. 6 is a cross-sectional view of an embodiment of the imaging system of the present invention showing the prostate endorectal probe operating in conjunction with upper and lower semi-cylindrical PET imaging detector panels (sectors).

FIG. 6 shows a preferred embodiment of the imaging system and probe of the present invention. FIG. 6 does not show the target organ and probe to scale and the drawing should be treated as showing the invention elements. In FIG. 6, the imaging system of this invention shows that PET detectors are made up of sixteen (16), in this example, external PET detector modules divided into two sectors: top and bottom, placed on an approximately cyclindrical surface, and the probe of this invention having the PET and ultrasound sensors. The probe is placed inside the external shield, as described herein, and the shield is then placed endorectally into the patient under the prostate. The probe's size permits that at any position of the probe, only a fraction of the lines of response of back-to-back coincident 511 keV annihilation gamma ray pairs between the front external PET detector modules and the probe of this invention, is recorded. The probe of this invention has a 6-parameter (3 coordinates and 3 angles) position probe that monitors and records positioning of the ultrasound/PET probe of this invention relative to the outside PET detector modules of the imaging system of this invention. Optionally, a temperature probe is included with the dual modality ultrasound and PET probe of this invention and the positioning probe to compensate the temperature-sensitive SiPMs.

FIG. 7 shows a side view of a preferred embodiment of the dual modality probe of this invention. In this preferred embodiment of the probe, the ultrasound sensor is placed in the front of the positron emission tomography sensor. The position sensor (probe), temperature sensor (probe), and a potential optical component are not shown.

Figure 8:
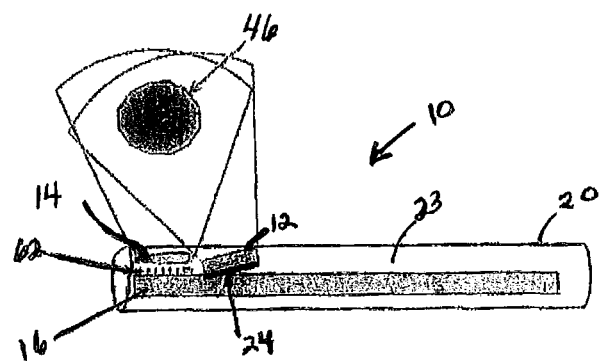
FIG. 8 is a side view of an embodiment of the probe of the present invention wherein the PET sensor is disposed at an angle within the housing of the probe.
Figure 9:
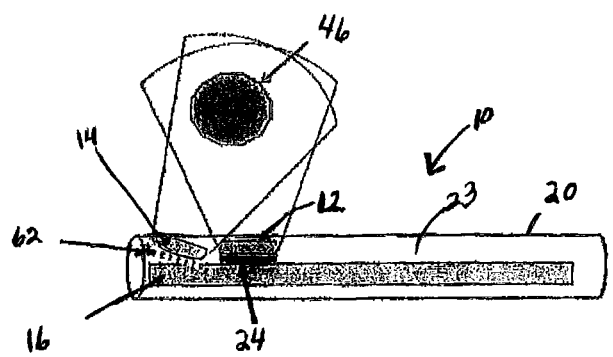
FIG. 9 is a side view of an embodiment of the probe of the present invention wherein the ultrasound sensor is disposed at an angle within the housing of the probe.

FIGS. 8 and 9 show different embodiments of the dual modality probe of the present invention. FIG. 8 shows the PET sensor is tilted within the housing of the probe and FIG. 9 shows that the ultrasound sensor is tilted within the housing of the probe, each for real time imaging of the same field view of a prostate gland. The 3D image fusion of both the ultrasound and PET of the present invention are much more accurate than any of the background art.

Figure 10:
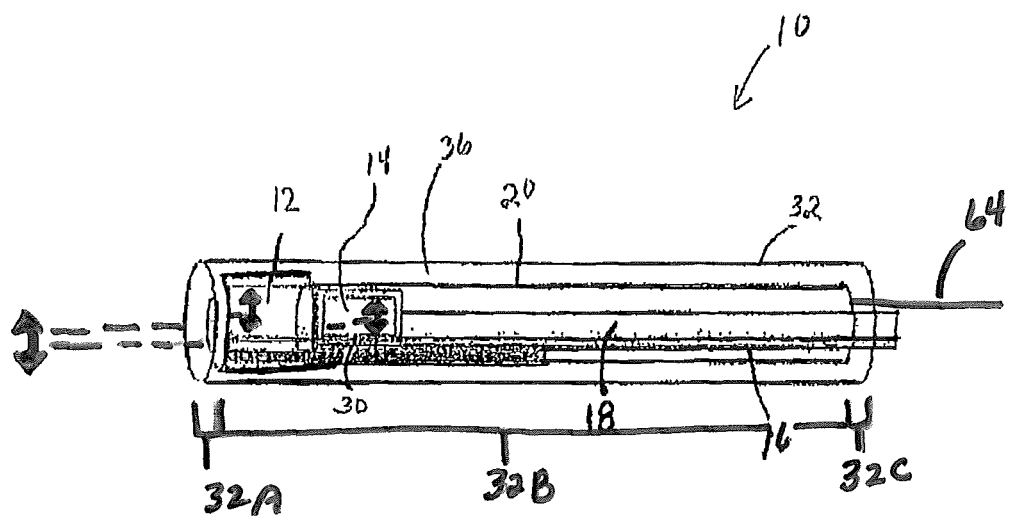
FIG. 10 is a side view of another embodiment of the probe of the present invention wherein the PET sensor is placed in front of the ultrasound sensor of the probe.

FIG. 10 shows another embodiment of the dual modality probe of the present invention with the optional external shield. The external shield is placed in the patient (rectum or other cavity) in a constant position at all times during the imaging system scan of this invention. The probe of this invention is inserted into the external shield and then the probe is moved inside the external shield during the scan and method of this invention. The presence of the external shield is exerting constant and stable pressure on the prostate and surrounding tissues and stabilizing the target organ and surrounding tissues during the method/scan of the present invention. In FIG. 10, the PET sensor element is placed in front of the ultrasound sensor element. To assure proper transmission of the ultrasound waves/signal, the ultrasound sensor is placed in a separate isolated compartment on a support board within the probe, and is optionally covered by a shield element, to allow application of proper coupling compound, such as for example, a gel, between the sensor and the outer shield. In addition, there will need to be ultrasound coupling compound between the shield and the patient's tissue.

Construction of the PET Sensor

Figure 11:
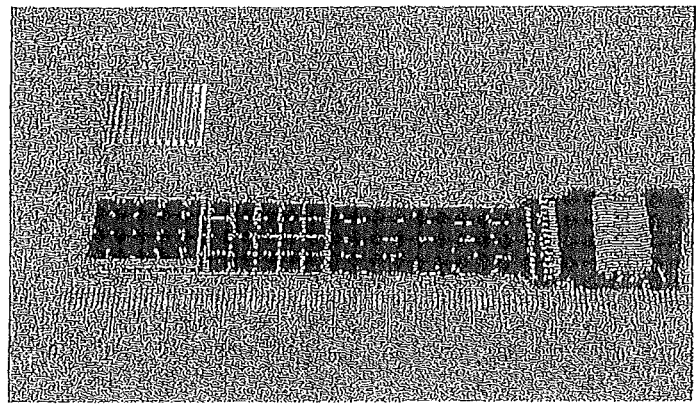
FIG. 11 is a top view of an embodiment of a PET sensor of the probe of the present invention.

FIG. 11 shows an embodiment of the PET sensor of the present invention, wherein a working PET sensor based upon an array of 4×10 MPCC (multipixel photon counter) SiPMs commercially available from Hamamatsu, with approximately 15 mm×45 mm active FOV. This particular sensor was equipped with 16×18 mm scintillator array shown at the top of FIG. 11, defining this as the active size of the PET probe. Amplifier and connector banks are in the handle region of the probe. The ultrasouns sensor can be either placed in front (preferred implementation) or behind the scintillator gamma sensor.

FIG. 12 shows another embodiment of a dual modality probe of the present invention. The size of this probe I, for example but not limited to, 3 cm wide by 2 cm tall. FIG. 12 A shows the photodetector sensor are built out of 72 MPPCs units commercially available from Hamamatsu arranged in a 6×12 array. The 3×3×mmm MPPC units were spaced at 5 mm center to center distance. In the center of the probe is the input stage electronics (amplifiers) and at the right is the bank of cable connectors matching with three small profile flat cables. FIG. 12 B shows a side view of the probe with a 1 cm thick LYSO array—which indeed shows how compact is the design of ther SiPM array. The thickness of the total assembly is practically defined bny the combined radiation sensor (scintillator) and the light guide (<20 mm). FIG. 12 C shows three key components of the probe of this embodiment. A light spreader window provides light sharing between individual MPPC units. LYSO array of 1.5×1.5×10 mm pixels (commercially available from Proteus). FIG. 12D shows a raw image obtained with the LYSO array coupled to to the MPPC array, demonstrating the desired intrinsic spatial resolution of 1.5 mm in this particular embodiment.

FIG. 13A shows another embodiment of the probe of the present invention that is 14 mm (millimeter) wide having a high resolution (1 mm) with a depth of interaction (DOI) capability. FIG. 13A shows a 1 mm pitch, 10 mm thick, 12×12 pixel LYSO (rare earth scintillator lutetium-yttrium oxyorthosilicate) scintillator array commercially available from Proteus, with 50 micron Luminor septa for DOI operation, coupled to the very low profile (<2 mm thick) SensL 16ch SPMArray2 module, shown from the top and side view. FIG. 13B shows a 1 mm DOI module during assembly with two SiPM modules coupled at both sides of the LYSOarray. Glass 2 mm thick windows are inserted between the arrays and SiPM modules. Sylgrad 3-6636 silicone gel was used as an optical coupling between all optical surfaces.

FIG. 14 A, FIG. 14B, and FIG. 15 show assembled dual modality probes of the present invention.

PET Imaging Agents

While this invention is not focusing on the imaging agents used to visualize the prostate cancer in PET modality, the issue of proper selection of PET imaging agent is important, as prostate cancer, unlike most of other cancers, is not avidly absorbing glucose analog—$^{18}$F—Flurodeoxyglucose (FDG}—used in the standard PET scans. In a recent paper, Mullani et al., First-Pass 18F-FDG PET of Blood Flow, The Journal of Nuclear Medicine, Volume 49, No. 4, April, 2008, the authors propose that even in the case of prostate cancer FDG will provide valid indication of prostate cancer, if used in the first-pass mode. Imaging is then performed in the first 2 minutes post-injection (first-pass blood flow procedure) and then repeated as a standard glucose uptake scan about 45-60 minutes later, so that two comparative images are obtained allowing for better identification of prostate cancer than with the standard glucose uptake image only. Therefore, we are specifically mentioning this unique method, as FDG is readily available in medical facilities and this fact will be a major enabler of the present invention, while also including other imaging agents such as Choline, and other prostate cancer specific imaging agents under development. Some examples are listed below (but are not limited to this list):

[$^{64/62/60}$Cu]ATSM/PTSM
$^{18}$F, $^{11}$C-labeled choline analogs
[$^{11}$C]acetate
[$^{18}$F]FMAU
16b-[$^{18}$F]fluoro-5a-dihydrotestosterone, etc.

The present invention relates generally to hybrid imaging dual modality (device) that functions to provide accurate localization of a target tumor or organ. The dual modality probe includes an ultrasound component to provide structural 3-D information related to the target tumor or organ, and a positron emission tomography (PET) component to provide metabolic information related to the biological state of the target tumor or organ. In particular, when used to image the prostate gland of a male patient, the dual modality imaging system of this invention may be used to specifically detect the presence of cancerous structures in the prostate, and may be adapted to identify cancerous structures showing increased metabolic activity. The imaging information obtained by using the present dual modality imaging system may be used to provide guidance for a biopsy procedure, for example, or for other medical procedures requiring surgical intervention.

FIG. 7 shows an embodiment of the dual modality probe 10 of the present invention. The probe 10 comprises a housing 20 having an external shell 21 and an interior space 23, the housing having a first end 25, a middle section 27, and a second end 29. The probe 10 has an ultrasound sensor 14, a positron emission tomography sensor (module) 12, a PET scintillator 22, PET detection electronics 26, a PET photoarray 24, a substrate or support board 16, and a cable set 18 for providing electrical power to the positron emission tomography sensor 12 and other PET components and the ultrasound sensor 14. The cable set 18 also includes a plurality of electrical conductors for transmitting signals between the positron emission tomography sensor 12, the ultrasound sensor 14, and a PET detector imaging and control unit (not shown). The probe 10 is in the configuration as shown in FIG. 7 as an endorectal imaging probe 10 combining the molecular modality of the positron emission tomography sensor 12 with the structural modality of the ultrasound sensor 14 in a single housing (enclosure) 20. The positron emission tomography sensor 12 may include a scintillator 22, a photodetector array 24 disposed adjacent the scintillator 22, and detection/control electronics 26 disposed adjacent the photodetector array 24. FIG. 7 shows that the dual modality probe of this invention includes an electronic sensor positioning system 62, wherein the electronic sensor positioning system has a first electronic sensor 63 located either on the exterior of the housing 20 of the probe 10 or within the interior space 23 of the housing 20 and a second electronic sensor (not shown in FIG. 7) located on or within one or more positron emission tomography detector heads (not shown in FIG. 7) such that the first electronic sensor 63 of the electronic positioning system 62 is in communication with the second electronic sensor of the electronic sensor positioning system wherein the electronic sensor positioning system spatially co-registers the probe 10 to each positron emission tomography detector head(s) (not shown in FIG. 7). FIG. 10 shows another embodiment of the probe 10 of the present invention wherein the PET sensor 12 is disposed in front of the ultrasound sensor 14. In this embodiment, an isolation compartment 30 is provided to partially or completely envelope the ultrasound sensor 14 to insure proper transmission of ultrasound signals to the prostate gland or other region of interest. FIG. 10 shows that in one embodiment of this invention the dual modality probe of this invention has an external shield 32. The external shield 32 has a first end 32A, an interior (middle section 32B), and a second end 32C, wherein the external shield 32 has an interior section that has a diameter that accommodates the dual modality probe 10 of this invention being inserted into the interior section 32B of the external shield 32, and wherein at least one of the first end 32A, or second end 32C of the external shield 32 is open such that the housing 20 of the probe 10 is freely movable within and outside of at least a portion of the external shield 32. Preferably, the housing 20 of this probe is movable for at least one of a lateral movement (i.e. horizontal movement) relative to a lateral plane of the external shield 32, a longitudinal movement (i.e. vertical movement) relative to a lateral plane of the external shield 32, or a transverse movement (i.e. an angular movement) relative to a lateral plane of the external shield 32, within and outside at least a portion of the external shield 32. More preferably, the probe 10 is in communication with a movement element 64 wherein the movement element controls the lateral, or longitudinal, or transverse movements of the probe 10 relative to a lateral plane of the shield, and within and outside at least a portion of the external shield 32. Optionally, the probe 10 may have a probe shield (not shown) that partially or completely covers the probe 10 and is positioned between the housing 20 of the probe 10 and the external shield 32. An ultrasound coupling compound 36 may be placed between the housing 20 of the probe 10 and the external shield 32. As stated hereinbefore, the external shield 32 may be placed into the patient, and maintained in a relatively constant position. The positron emission tomography sensor 12 and the ultrasound sensor 14 may then be moved inside of the external shield 32 during the scanning and imaging procedure. FIGS. 7 and 10 show that the ultrasound sensor 14 is disposed within the interior space 23 of the housing 20 such that the ultrasound sensor 14 is rotatable about a first axis of rotation and that the positron emission tomography sensor 12 is disposed within the interior space 23 of the housing 20 such that the positron emission tomography sensor is rotatable about a second axis of rotation. The external shield 32 may thus function to exert a relatively constant and stable pressure on the prostate gland and surrounding tissue. This exertion of pressure enables the prostate endorectal probe 10 to substantially remain in position during an imaging scan. A software module (not shown) may provide advanced image and signal processing techniques for tissue classifications. Additional capabilities may provide for signal processing in the time domain, in the frequency domain, and in the wavelet domain, as is well known in the relevant art.

FIG. 5 shows another embodiment of the present invention of the imaging system of the present invention including a first PET detector head 40, a second PET detector head 41, a bed 42 for the patient to lie on, a PET response signal 44, and the external shield 32 of the probe 10 (not shown) inserted into the external shield 32. The patient's torso 48 and the prostate gland of a male patient 46 are also shown. FIG. 6 shows another embodiment of the imaging system of the present invention including a first set of external PET detectors 50 (eight such PET detectors) shown on top of a patient's body 48 (torso), a second set of external PET detectors 52 (eight such PET detectors) shown on the bottom or underneath of the patient's body 48, wherein each of the first and second sets of external PET detectors are mounted to a mobile gantry (not shown), probe 10 of the present invention (as previously described herein) inside the external shield 32.

FIG. 8 shows an embodiment of the present invention wherein the ultrasound sensor 14 comprises a two-dimensional piezoelectric crystals array 62 used to produce three-dimensional ultrasound images. In the configuration shown in FIG. 8, the piezoelectric crystal array 62 may be immovably fixed to the substrate 16 (backing material). The substrate 16 and additional layers of substrate may be provided. In an exemplary embodiment, the ultrasound sensor 14 module 64 may operate at a frequency range of from about 2.50 MHz to about 15.0 MHz, with a field of view ranging from about 30.0 mm to about 150 mm. FIG. 8 shows the PET sensor tilted within the interior 23 of the housing 20 of the probe 10. In yet another embodiment of the present invention, FIG. 9 shows the probe 10 of this invention wherein the ultrasound sensor 14 and the piezoelectric crystal array 62 are tilted within the interior 23 of the housing 20 of the probe 10. FIG. 9 shows that the ultrasound sensor 14 and the piezoelectric crystal array 62 may be rotated to more directly face the prostate gland 46 (or prostate cancer).

FIG. 16 shows an exemplary embodiment of a positron emission tomography sensor 12. In the configuration shown in FIG. 16, the positron emission tomography sensor 12 comprises a photodetector array 24 disposed on a substrate 16. A protective window 70 may be disposed between the photodetector array 24 and a scintillator 22. A collimator 72 may be provided on the scintillator 22 for improving the acquisition of positron emissions from the region of interest. The positron emission tomography sensor 12 may be disposed on a substrate 16 adjacent an ultrasound sensor 14, as shown in FIG. 17, to form a prostate endorectal probe 12. Positioning sensors (not shown) may be used to determine the position of the prostate endorectal probe 12, and to register the image obtained from the photodetector array 24 with the image obtained from the positron emission tomography sensor 12 so as to obtain a 3-D image of the region of interest.

It is understood by one skilled in the art that a standard positron emission tomography scanner typically offers a spatial resolution of only about 5 mm, at best. This precision is not adequate to show details of uptake in small organs such as the prostate gland. Accordingly, the present invention provides a combination of high-resolution positron emission tomography with new imaging markers. This novel combination provides for a highly improved molecular imaging system and method for the detection of prostate cancer.

Recent developments in the field of compact Silicon Photomultipliers (SiPMs), have enabled the fabrication of a positron emission tomography module that operates with high resolution PET detectors (see FIGS. 5 and 6) to provide a resolution on the order of one millimeter. Such resolution in the present mobile imaging system enables the imaging of the prostate gland. The implemented US sensor will possess optimized tissue differentiating capability, maximizing the molecular differentiating power of the PET/TDUS hybrid system. Prostate PET with new imaging agents has high molecular imaging power, but it is not providing high resolution anatomic information necessary for biopsy or surgical assistance. Standard ultrasound may not be adequately tissue-specific to distinguish between a cancer and normal tissue. However, the disclosed dual modality probe and imaging system of the present invention combines the best features of the two modalities to allow for the early detection and biopsy guidance of cancerous prostatic lesions.

In an exemplary embodiment of the present invention, FIG. 19 shows a positron emission tomography sensor 12 may comprise compact silicon photomultipliers and pixelated scintillators. Scintillator materials may comprise CsI (TI), CsI(Na), GSO, NaI(TI), and LaBr3. A tungsten composite may be used for a collimator material. The scintillators function to: (i) detect incident radiation comprising 511 KeV annihilation gammas from positron emissions in the prostate gland, and (ii) convert the incident radiation conversion into scintillation signals. The scintillation signals are, in turn, detected by the silicon photomultipliers and provided to detection/control electronics 102. An ultrasound sensor 14 secured to a substrate 16 may be located ahead of the positron emission tomography sensor 12, and contained in a housing 20 with the positron emission tomography sensor 12.

FIG. 19 shows an embodiment of the method of evaluating a target organ (such as the prostate gland of a male patient) of the present invention with the dual modality probe and imaging system of the present invention with the steps of this method illustrated in a flow diagram.

Those persons skilled in the art will understand that changes could be made to the embodiments described above without departing from the inventive concept of the probe, the imaging system, and methods of the present invention. The accompanying drawings are included to provide a further understanding of various features and embodiments of the probe, imaging system, and methods of the invention which, together with their description serve to explain the principles and operation of the invention set forth herein. It is understood, therefore, that this invention is not limited to the particular embodiments disclosed, but is intended to cover modifications that are within the spirit and scope of the invention, as defined by the appended claims.

We claim:
1. A dual modality probe comprising:
   a housing having an external shell and an interior space, said housing having a first end, a middle section, and a second end, wherein said middle section is disposed between said first and said second ends, and wherein said second end is opposite said first end;
   an ultrasound sensor located within the first end of said interior of said housing wherein said ultrasound sensor provides a 3D ultrasound image;

a positron emission tomography sensor located within said first end of said interior of said housing and wherein said positron emission tomography sensor is located in juxtaposition to said ultrasound sensor within said interior of said housing, wherein said positron emission tomography sensor consisting essentially of an array of multipixel photon counters and a rare earth scintillator lutetium-yttrium oxyorthosilicate array having a 1 millimeter resolution with septa for depth of interaction operation wherein said rare earth scintillator lutetium-yttrium oxyorthosilicate array is coupled to said array of multipixel photon counters for three-dimensional spatial resolution, wherein said positron emission tomography sensor provides a 3D positron emission tomography image, and a software module configured to implement a fusion algorithm to fuse said 3D ultrasound image with said 3D positron emission tomography image; and a temperature probe comprising one or more temperature sensors with bias voltage feedback to compensate for temperature sensitivity of said positron emission tomography sensor, and wherein said ultrasound sensor is disposed within said interior of said housing such that it is rotatable about a first axis of rotation within said housing, and wherein said positron emission tomography sensor is disposed within said interior of said housing such that it is rotatable about a second axis of rotation within said housing.

2. The dual modality probe of claim 1 further comprising an electronic sensor positioning system having at least one first electronic sensor, at least one second electronic sensor, and a positron emission tomography imager with one or more positron emission tomography detector heads, wherein said at least one first electronic sensor is located either on said external shell of said housing of said probe or within said interior of said housing, wherein said at least one first electronic sensor is configured to be in communication with said at last one second electronic sensor, wherein said at least one second electronic sensor is located on or within said one or more positron emission tomography detector heads, wherein said electronic sensor positioning system is configured to spatially co-register said probe to each positron emission tomography detector head.

3. The dual modality probe of claim 1 including an external shield that has a first end and a second end that is disposed opposite said first end, said external shield having an interior section, said interior section having a diameter that accommodates said probe to be inserted into the interior section of said external shield, and wherein at least one of said first end or second end of said shield is open such that said housing of said probe is movable within and outside of at least a portion of said external shield.

4. The dual modality probe of claim 3 wherein said housing of said probe is movable for at least one of a lateral movement, a longitudinal movement, or a transverse movement relative to a lateral plane of said external shield.

5. The dual modality probe of claim 4 further comprising a movement element in communication with said probe, said movement element configured to control said lateral, or longitudinal, or transverse movements of said probe relative to said lateral plane of said external shield and within and outside of at least a portion of said external shield.

6. The dual modality probe of claim 1 wherein said ultrasound sensor is disposed more proximally within said housing than is said positron emission tomography sensor.

7. The dual modality probe of claim 1 wherein said ultrasound sensor is disposed within said housing to be more proximal to said second end of said housing than is said positron emission tomography sensor.

8. The dual modality probe of claim 7, including an isolation compartment located within said housing for enclosing either partially or completely said ultrasound sensor within said housing from said positron emission tomography sensor.

9. The dual modality probe of claim 8 wherein a support board is disposed within said housing and wherein said ultrasound sensor, said positron emission tomography sensor, and said isolation compartment are positioned on said support board within said housing.

10. The dual modality probe of claim 1 wherein a support board is disposed within said housing and wherein said ultrasound sensor and said positron emission tomography sensor are positioned on said support board within said housing.

11. The dual modality probe of claim 1 including a biopsy gun attached to the external shell of said housing of said probe, said biopsy gun equipped with a biopsy needle.

12. A mobile dual modality imaging system comprising:
a bed for accommodating a patient;
an open rotating gantry mounted around said bed and mobile with respect to said bed;
a positron emission tomography imager having at least one positron emission tomography detector head secured to said rotating gantry above said bed and at least one positron emission tomography detector head secured to said rotating gantry below said bed, wherein each of said detector heads is capable of angular rotation with respect to said bed;
a probe comprising a housing having an external shell and an interior space, said housing having a first end, a middle section, and a second end, wherein said middle section is disposed between said first and said second ends, and wherein said second end is opposite said first end, an ultrasound sensor located within the first end of said interior of said housing wherein said ultrasound sensor provides a 3D ultrasound image, and a positron emission tomography sensor located within said first end of said interior of said housing and wherein said positron emission tomography sensor is located in juxtaposition to said ultrasound sensor within said interior of said housing, wherein said positron emission tomography sensor consisting essentially of an array of multipixel photon counters and a rare earth scintillator lutetium-yttrium oxyorthosilicate array having a 1 millimeter resolution with septa for depth of interaction operation wherein said rare earth scintillator lutetium-yttrium oxyorthosilicate array is coupled to said array of multipixel photon counters for three-dimensional spatial resolution, wherein said positron emission tomography sensor provides a 3D positron emission tomography image, and a software module configured to implement a fusion algorithm to fuse said 3D ultrasound image with said 3D positron emission tomography image, said positron emission tomography sensor having a first diameter and said ultrasound sensor having a second diameter, and said external shell of said housing having a third diameter, wherein each of said first diameter of said positron emission tomography sensor and said second diameter of said ultrasound sensor is less than said third diameter of said external shell of said housing, and wherein said ultrasound sensor of said probe is disposed within said interior of said housing such that it is rotatable about a first axis of rotation within said housing and wherein said positron emission tomography sensor of said probe is disposed within said interior of said housing such that it is rotatable about a second axis of rotation within said housing;

a temperature probe comprising one or more temperature sensors with bias voltage feedback to compensate for temperature sensitivity of said positron emission tomography sensor, and an electronic sensor positioning system having at least one first electronic sensor and at least one second electronic sensor, wherein said at least one first electronic sensor is located either on said external shell of said housing of said probe or within said interior of said housing, wherein said at least one second electronic sensor is located on or within each of said positron emission tomography detector heads such that said at least one first electronic sensor of said electronic sensor positioning system is configured to be in communication with said at least one second electronic sensor of said electronic sensor positioning system wherein said electronic sensor positioning system is configured to spatially co-register said probe to each detector head; and a data acquisition computer system for collecting data simultaneously from said positron emission tomography sensor and said ultrasound sensor of said probe and said positron emission tomography imager, wherein said rotating gantry enables 360 degree angular sampling in a 3D imaging mode with said probe and said positron emission tomography imager.

13. The dual modality imaging system of claim 12 wherein each of said detector heads is configured to operate in at least one of a fixed position with respect to a target organ of a patient lying on said bed and a rotational position such that said detector head is rotated with respect to the target organ of the patient lying on said bed.

14. The dual modality imaging system of claim 12 wherein said ultrasound sensor is disposed more proximally within said housing than is said positron emission tomography sensor.

15. The dual modality imaging system of claim 12 wherein said ultrasound sensor is disposed within said housing to be more proximal to said second end of said housing than is said positron emission tomography sensor.

16. The dual modality imaging system of claim 15 including an isolation compartment located within said housing of said probe for enclosing either partially or completely said ultrasound sensor within said housing from said positron emission tomography sensor.

17. The dual modality imaging system of claim 16 wherein a support board is disposed within said housing and wherein said ultrasound sensor, said positron emission tomography sensor, and said isolation compartment of said probe are positioned on said support board within said housing of said probe.

18. The dual modality imaging system of claim 12 wherein a support board is disposed within said housing and wherein said ultrasound sensor and said positron emission tomography sensor of said probe are positioned on said support board within said housing of said probe.

19. A method for evaluating a target organ of a patient comprising:
injecting a patient with an imaging agent;
providing a mobile dual modality imaging system comprising:

a bed for accommodating a patient, an open rotating gantry mounted around said bed and mobile with respect to said bed, a positron emission tomography imager having at least one positron emission tomography detector head secured to said rotating gantry above said bed and at least one positron emission tomography detector head secured to said rotating gantry below said bed, wherein each of said positron emission tomography detector head is capable of angular rotation with respect to said bed, a probe comprising a housing having an external shell and an interior space, said housing having a first end, a middle section, and a second end, wherein said middle section is disposed between said first and said second ends, and wherein said second end is opposite said first end, an ultrasound sensor located within the first end of said interior of said housing wherein said ultrasound sensor provides a 3D ultrasound image, and a positron emission tomography sensor located within said first end of said interior of said housing and wherein said positron emission tomography sensor is located in juxtaposition to said ultrasound sensor within said interior of said housing, wherein said positron emission tomography sensor consisting essentially of an array of multipixel photon counters and a rare earth scintillator lutetium-yttrium oxyorthosilicate array having a 1 millimeter resolution with septa for depth of interaction operation wherein said rare earth scintillator lutetium-yttrium oxyorthosilicate array is coupled to said array of multipixel photon counters for three-dimensional spatial resolution, wherein said positron emission tomography sensor provides a 3D positron emission tomography image when operating in conjunction with said positron emission tomography imager, said positron emission tomography sensor having a first diameter and said ultrasound sensor having a second diameter, and said external shell of said housing having a third diameter, wherein each of said first diameter of said positron emission tomography sensor and said second diameter of said ultrasound sensor is less than said third diameter of said external shell of said housing, and wherein said ultrasound sensor of said probe is disposed within said interior of said housing such that it is rotatable about a first axis of rotation within said housing and wherein said positron emission tomography sensor of said probe is disposed within said interior of said housing that it is rotatable about a second axis of rotation within said housing, an electronic sensor positioning system having at least one first electronic sensor and at least one second electronic sensor, wherein said at least one first electronic sensor is located either on said external shell of said housing of said probe or within said interior of said housing, wherein said at least one second electronic sensor is located on or within each of said positron emission tomography detector head such that said at least one first electronic sensor of said electronic sensor positioning system is in communication with said at least one second electronic sensor of said electronic sensor positioning system wherein said electronic sensor positioning system spatially co-registers said probe to said detector head, and a data acquisition computer system for collecting data simultaneously from said positron emission tomography sensor and said ultrasound sensor of said probe and said positron emission tomography imager; and a software module configured to implement a fusion algorithm to fuse said 3D ultrasound image with said 3D positron emission tomography image;

compensating for temperature sensitivity of said positron emission tomography sensor via a temperature probe comprising one or more temperature sensors with bias voltage feedback;

positioning said patient on said bed of said dual modality imaging system;

operating said dual modality imaging system such that said dual modality imaging system is positioned to scan a target organ of said patient; and generating a 360 degree angular sampling with said open rotating gantry in a 3D imaging mode with said probe and said positron emission tomography imager.

20. The method of claim 19 including positioning a biopsy gun on said external shell of said housing of said probe for conducting a biopsy of said target organ.

\* \* \* \* \*